US00PP27008P2

(12) United States Plant Patent
Sakazaki

(10) Patent No.: US PP27,008 P2
(45) Date of Patent: Aug. 2, 2016

(54) *CALIBRACHOA* PLANT NAMED 'USCAL42202'

(50) Latin Name: ***Calibrachoa* sp.**
Varietal Denomination: USCAL42202

(71) Applicant: Ushio Sakazaki, Shiga (JP)

(72) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 115 days.

(21) Appl. No.: 14/121,651

(22) Filed: Oct. 1, 2014

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — C. A. Whealy

(57) ABSTRACT

A new and distinct *Calibrachoa* plant named 'USCAL42202', characterized by its compact, upright to outwardly spreading and mounding plant habit; freely branching habit; dense and bushy appearance; freely flowering habit; violet-colored flowers with central purple-colored star pattern and yellow-colored throats; and good garden performance.

1 Drawing Sheet

Botanical designation: *Calibrachoa* sp.
Cultivar denomination: 'USCAL42202'.

BACKGROUND OF THE INVENTION

The present invention relates to a new and distinct cultivar of *Calibrachoa* plant, botanically known as *Calibrachoa* sp. and hereinafter referred to by the name 'USCAL42202'.

The new *Calibrachoa* plant is a product of a planned breeding program conducted by the Inventor in Higashiomi, Shiga, Japan and Bonsall, Calif. The objective of the breeding program is to create new uniform and freely-branching *Calibrachoa* plants with unique and attractive flower coloration and good garden performance.

The new *Calibrachoa* plant originated from a cross-pollination made by the Inventor on May 8, 2011 in Higashiomi, Shiga, Japan of a proprietary seedling selection of *Calibrachoa* sp. identified as code number 11CJ22-03, not patented, as the female, or seed, parent with a proprietary seedling selection of *Calibrachoa* sp. identified as code number 11CJ32-01, not patented, as the male, or pollen, parent. The new *Calibrachoa* plant was discovered and selected by the Inventor as a single flowering plant within the progeny of the stated cross-pollination in a controlled environment in Bonsall, Calif. on May 24, 2012.

Asexual reproduction of the new *Calibrachoa* plant by terminal cuttings in a controlled environment in Bonsall, Calif. since May 25, 2012 has shown that the unique features of this new *Calibrachoa* plant are stable and reproduced true to type in successive generations.

SUMMARY OF THE INVENTION

Plants of the new *Calibrachoa* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'USCAL42202'. These characteristics in combination distinguish 'USCAL42202' as a new and distinct *Calibrachoa* plant:

1. Compact, upright to outwardly spreading and mounding plant habit.
2. Freely branching habit; dense and bushy appearance.
3. Freely flowering habit.
4. Violet-colored flowers with central purple-colored star pattern and yellow-colored throats.
5. Good garden performance.

The new *Calibrachoa* plant can be compared to plants of the female parent selection. Plants of the new *Calibrachoa* differ primarily from plants of the female parent selection in flower color as plants of the female parent selection have purplish pink-colored flowers.

The new *Calibrachoa* plant can be compared to plants of the male parent selection. Plants of the new *Calibrachoa* differ primarily from plants of the male parent selection in flower color as plants of the male parent selection have brownish purple-colored flowers.

Plants of the new *Calibrachoa* can be compared to plants of the *Calibrachoa* sp. 'USCAL91001', disclosed in U.S. Plant Pat. No. 23,232. In side-by-side comparisons conducted in Bonsall, Calif., plants of the new *Calibrachoa* differed primarily from plants of 'USCAL91001' in flower color as plants of 'USCAL91001' had red purple-colored flowers with yellow-colored star-shaped pattern and centers.

Plants of the new *Calibrachoa* can also be compared to plants of the *Calibrachoa* sp. 'USCAL56501', disclosed in U.S. Plant Pat. No. 21,628. In side-by-side comparisons conducted in Bonsall, Calif., plants of the new *Calibrachoa* differed primarily from plants of 'USCAL56501' in flower color as plants of 'USCAL56501' had violet-colored flowers with darker violet-colored centers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet comprises a side perspective view of a typical flowering plant of 'USCAL42202' grown in a container.

The photograph at the top of the sheet is a close-up view of a typical flowering plant of 'USCAL42202'.

DETAILED BOTANICAL DESCRIPTION

The aforementioned photographs and following observations, measurements and values describe plants grown during the spring in 11.5-cm containers in a polyethylene-covered greenhouse and subsequently in an outdoor nursery in Bonsall, Calif. During the production of the plants, day temperatures averaged 24° C. and night temperatures ranged from 13° C. to 16° C. Plants were pinched two times and were six weeks old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL42202'.

Parentage:

*Female, or seed, parent*.—Proprietary seedling selection of *Calibrachoa* sp. identified as code number 11CJ22-03, not patented.

*Male, or pollen, parent*.—Proprietary seedling selection of *Calibrachoa* sp. identified as code number 11CJ32-01, not patented.

Propagation:

*Type*.—By terminal cuttings.

*Time to initiate roots, summer*.—About four days at temperatures ranging from 17° C. to 29° C.

*Time to initiate roots, winter*.—About six days at temperatures ranging from 17° C. to 21° C.

*Time to produce a rooted plant, summer*.—About 22 days at temperatures ranging from 16° C. to 29° C.

*Time to produce a rooted plant, winter*.—About 25 days at temperatures ranging from 16° C. to 21° C.

*Root description*.—Medium in thickness, fibrous; white in color.

*Rooting habit*.—Freely branching; medium density.

Plant description:

*Plant and growth habit*.—Compact, upright to outwardly spreading and mounding plant habit; freely branching habit with about twelve primary lateral branches each with multiple secondary branches; pinching enhances branching; dense and bushy appearance; vigorous growth habit.

*Plant height*.—About 11 cm.

*Plant diameter*.—About 22.5 cm.

Lateral branch description:

*Length*.—About 12.5 cm.

*Diameter*.—About 2 mm.

*Internode length*.—About 1.8 cm.

*Strength*.—Strong.

*Aspect*.—Initially upright then outwardly spreading to mounding.

*Texture*.—Pubescent; minute.

*Color*.—Close to 144A.

Leaf description:

*Arrangement*.—Before flowering, alternate; after flowering, opposite; leaves simple.

*Length*.—About 3 cm.

*Width*.—About 1.2 cm.

*Shape*.—Elliptical.

*Apex*.—Broadly acute to rounded.

*Base*.—Attenuate.

*Margin*.—Entire.

*Texture, upper and lower surfaces*.—Pubescent; minute.

*Venation pattern*.—Pinnate; arcuate.

*Color*.—Developing leaves, upper and lower surfaces: Close to 137B. Fully expanded leaves, upper surface: Close to 146A; venation, close to 146C. Fully expanded leaves, lower surface: Close to 147B; venation, close to 146D.

*Petioles*.—Length: About 3 mm. Diameter: About 2 mm. Texture, upper and lower surfaces: Pubescent; minute. Color, upper and lower surfaces: Close to 146C.

Flower description:

*Flower type and flowering habit*.—Single salverform flowers arising from leaf axils; freely flowering habit with typically about nine open flowers per lateral branch and more than 500 developing per plant; flowers face upright to outwardly.

*Fragrance*.—None detected.

*Natural flowering season*.—Plants of the new *Calibrachoa* begin flowering about four weeks after planting; plants flower continuously from spring though the summer until autumn in Southern California.

*Flower longevity*.—Individual flowers last about three to four days on the plant; flowers persistent.

*Flower buds*.—Length: About 2.2 cm. Diameter: About 7 mm. Shape: Oblong. Color: Close to 85B.

*Flower diameter*.—About 2.4 cm by 2.5 cm.

*Flower length* (*height*).—About 2.3 cm.

*Flower throat diameter*.—About 6 mm by 8 mm.

*Flower tube length*.—About 1.8 cm.

*Flower tube diameter, base*.—About 2.5 mm.

*Corolla*.—Arrangement: Five fused petals opening into a flared trumpet. Petal lobe length (from throat): About 1 cm. Petal lobe width: About 1.2 cm. Petal shape: Obovate. Petal apex: Rounded. Petal margin: Entire. Petal texture, upper surface: Smooth, glabrous; velvety. Petal texture, lower surface: Pubescent; minute, along veins. Throat texture: Smooth, glabrous. Tube texture: Pubescent; minute. Color: Petal lobe, when opening, upper surface: Close to N87B. Petal lobe, when opening, lower surface: Close to 85C. Petal lobe, fully opened, upper surface: Close to 86C; towards the throat, star pattern close to N79A; venation, close to 86B; color becoming closer to 86D with development. Petal lobe, fully opened, lower surface: Close to 85C; venation, close to N79A. Throat: Close to 13A; venation, close to 194B. Tube: Close to 162B; venation, close to N79B.

*Calyx*.—Arrangement: One star-shaped calyx tube with five sepals fused towards the base and arranged in a single whorl. Sepal length: About 1.4 cm. Sepal width: About 3 mm. Sepal shape: Elliptic. Sepal apex: Acute. Sepal margin: Entire. Sepal texture, upper and lower surfaces: Pubescent; minute. Sepal color, upper and lower surfaces: Close to 146A.

*Peduncles*.—Length: About 1.7 cm. Diameter: About 1 mm. Angle: About 45° to 55° from stem axis. Strength: Strong. Texture: Pubescent; minute. Color: Close to 146C.

*Reproductive organs*.—Stamens: Quantity: Five per flower. Filament length: About 8 mm. Filament color: Close to 145D. Anther length: About 1 mm. Anther shape: Round. Anther color: Close to 4C. Pollen amount: Moderate. Pollen color: Close to 4B. Pistils: Quantity: One per flower. Pistil length: About 9 mm. Style length: About 7 mm. Style color: Close to 145D. Stigma shape: Round. Stigma color: Close to 145B. Ovary color: Close to 145C. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'USCAL42202' as illustrated and described.

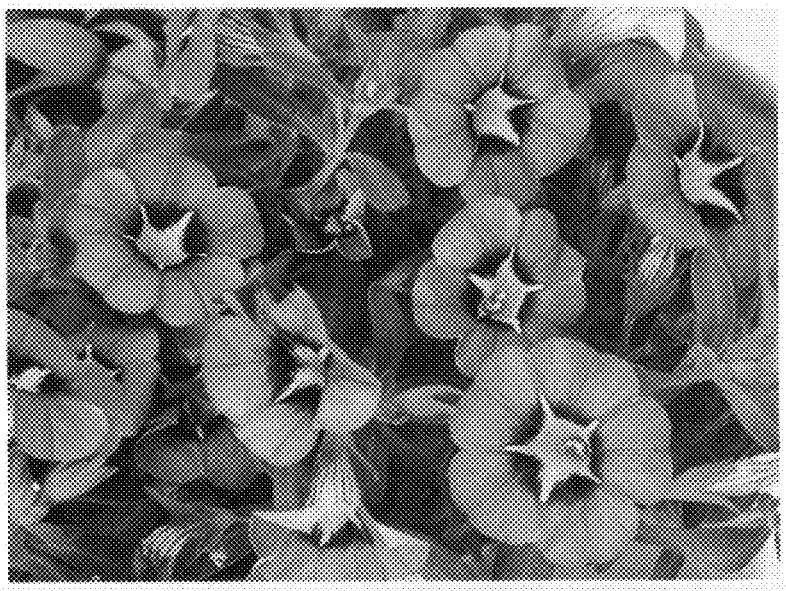
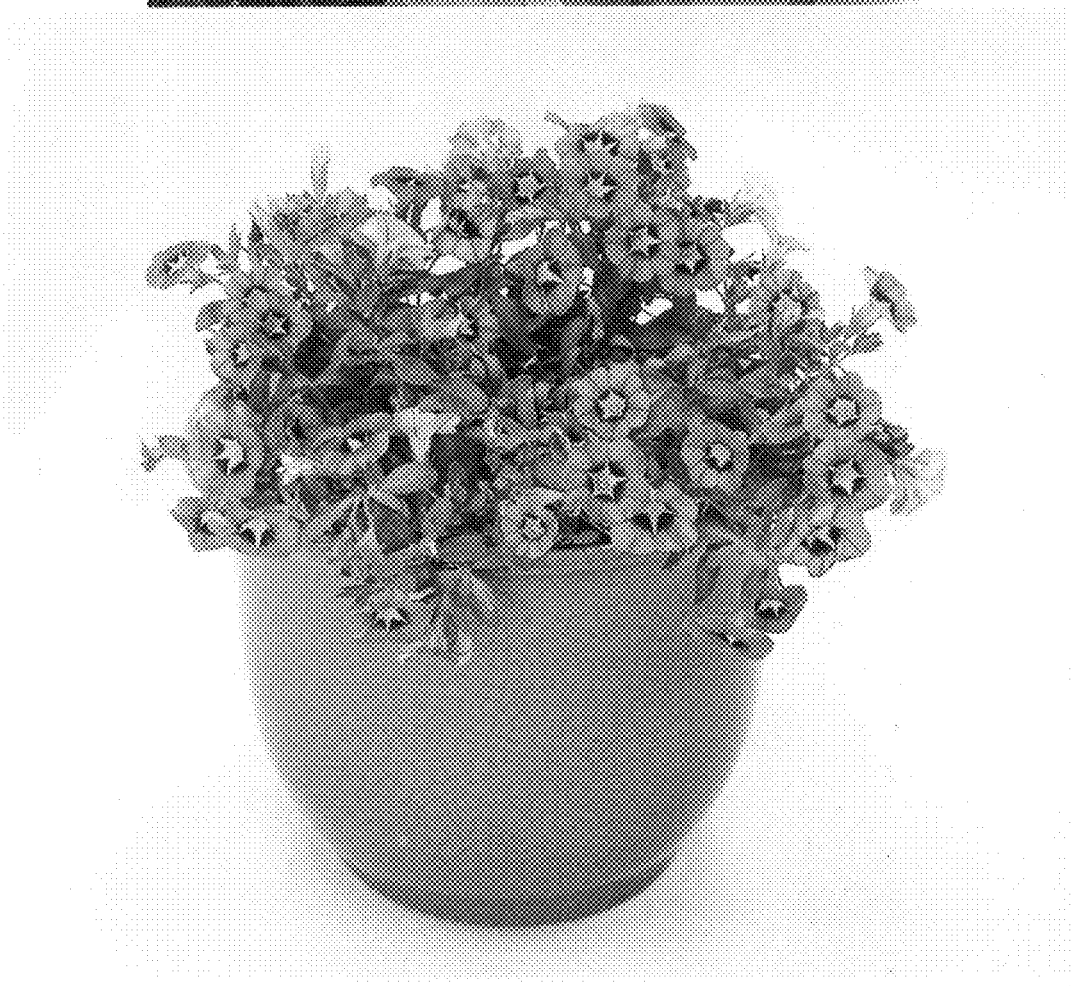

* * * * *